US008343950B2

(12) United States Patent
Tung

(10) Patent No.: US 8,343,950 B2
(45) Date of Patent: Jan. 1, 2013

(54) QUINAZOLINE DERIVATIVES AND METHODS OF TREATMENT

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 578 days.

(21) Appl. No.: 11/957,442

(22) Filed: Dec. 15, 2007

(65) Prior Publication Data

US 2008/0166358 A1 Jul. 10, 2008

Related U.S. Application Data

(60) Provisional application No. 60/875,320, filed on Dec. 15, 2006.

(51) Int. Cl.
*A61K 31/33* (2006.01)
(52) U.S. Cl. .................................................. 514/183
(58) Field of Classification Search .................. 514/183
See application file for complete search history.

(56) References Cited

U.S. PATENT DOCUMENTS

| | | | | |
|---|---|---|---|---|
| 3,138,542 | A * | 6/1964 | Von Polnitz et al. | 435/216 |
| 5,747,498 | A | 5/1998 | Schnur et al. | |
| 6,221,335 | B1 | 4/2001 | Foster | |
| 6,440,710 | B1 | 8/2002 | Keinan et al. | |
| 6,603,008 | B1 | 8/2003 | Ando et al. | |
| 6,900,221 | B1 | 5/2005 | Norris et al. | |
| 7,517,990 | B2 | 4/2009 | Ito et al. | |
| 2005/0272737 | A1 | 12/2005 | Chen et al. | |
| 2007/0082929 | A1 | 4/2007 | Gant et al. | |
| 2007/0197695 | A1 | 8/2007 | Potyen et al. | |
| 2008/0103122 | A1 | 5/2008 | Veltri | |
| 2009/0076042 | A1 | 3/2009 | Czarnik | |

FOREIGN PATENT DOCUMENTS

| | | |
|---|---|---|
| WO | WO-95/26325 | 10/1995 |
| WO | WO 96/30347 | * 10/1996 |

OTHER PUBLICATIONS

Ling et al., "Metabolism and Excretion of Erlotinib, A Small Molecule Inhibitor of Epidermal Growth Factor Receptor Tyrosine Kinase, in Healthy Male Volunteers", Drug Metabolism and Disposition, 34; 420-426, 2006.
Kushner, et al., "Pharmacological uses and perspectives of heavy water and deuterated compounds", Can. J. Physiol. Pharmacol. 77: 79-88 (1999).
Fisher et al., The complexities inherent in attempts to decrease drug clearance by blocking sites of CYP-mediated metabolism. Curr Opin Drug Discov Devel. 9(1): 101-9 (2006).
Prescribing information for TARCEVA® (erlotinib), accessed at http://www.fda.gov/cder/foi/label/2008/021743s010lbl.pdf (revised Aug. 2008).
International Search Report and Written Opinion for corresponding PCT Application No. PCT/US07/87689.
Foster, A.B., "Deuterium isotope effects in studies of drug metabolism", TIPS 524-527 (Dec. 1984).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551-559 (1987).
Browne, T.R., Journal of Clinical Pharmacology 38: 213-220 (1998).
Baillie, T.A., Pharmacology Rev. 33:81-132 (1981).
Foster, A.B., Adv Drug Res, 14:1-40 (1985).

* cited by examiner

*Primary Examiner* — Brandon Fetterolf
*Assistant Examiner* — Christopher R Stone
(74) *Attorney, Agent, or Firm* — Edwards Wildman Palmer LLP; Jeffrey D. Hsi; Mark D. Russett

(57) ABSTRACT

This invention relates to novel quinazoline derivatives, and their pharmaceutically acceptable salts. The invention also provides compositions comprising a compound of this invention and the use of such compositions in methods of treating diseases and conditions beneficially treated by inhibiting cell surface tyrosine receptor kinases.

12 Claims, No Drawings

QUINAZOLINE DERIVATIVES AND METHODS OF TREATMENT

CROSS-REFERENCE TO RELATED APPLICATIONS

This application claims the benefit of U.S. Provisional Patent Application No. 60/875,320, filed Dec. 15, 2006, the contents of which are incorporated herein by reference.

TECHNICAL FIELD OF THE INVENTION

This invention relates to novel quinazoline derivatives, and their pharmaceutically acceptable salts. The invention also provides compositions comprising a compound of this invention and the use of such compositions in methods of treating diseases and conditions beneficially treated by inhibiting cell surface tyrosine receptor kinases.

Quinazoline derivatives which bear at the 4-position an anilino substituent and which also bear an alkoxy substituent at the 7-position and an alkoxy substituent at the 6-position, are disclosed at least in U.S. Pat. No. 5,747,498, EP 1,110,953, EP 817,775, and U.S. Pat. No. 6,476,040. One of those derivatives, erlotinib, is known chemically as [6,7-Bis-(2-methoxy-ethoxy)-quinazolin-4-yl]-(3-ethynyl-phenyl)-amine and as N-(3-ethynylphenyl)-6,7-bis(2-methoxyethoxy)quinazolin-4-amine.

Erlotinib is an inhibitor of tyrosine kinases, particularly EGF receptor tyrosine kinases. Erlotinib has been approved in the United States in and in Europe for the treatment of locally advanced or metastatic non-small cell lung cancer (NSCLC) after failure of at least one prior chemotherapy regimen. Erlotinib is also approved in the United States in combination with gemcitabine, for the treatment of metastatic pancreatic cancer. Clinical trials are ongoing investigating the use of erlotinib alone or in combination with other agents for the treatment of a variety of cancers, including non-small cell lung cancer, ovarian cancer, colorectal cancer, head and neck cancer, brain cancer, bladder cancer, sarcoma, prostate cancer, melanoma, cervical cancer, solid tumors, astrocytoma, breast cancer, pancreatic cancer, glioblastoma multiform, renal cancer, digestive/gastrointestinal cancer, liver cancer, and gastric cancer. Erlotinib is also thought to be useful in the treatment of benign hyperplasia of the skin (psoriasis) or prostate (BPH).

Despite the beneficial activities of erlotinib, there is a continuing need for new compounds to treat the aforementioned diseases and conditions.

DEFINITIONS

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of erlotinib will inherently contain small amounts of deuterated and/or $^{13}$C-containing isotopologues. The concentration of naturally abundant stable hydrogen and carbon isotopes, notwithstanding this variation, is small and immaterial with respect to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

In one embodiment, a compound of the invention contains less than 10%, preferably less than 6%, and more preferably less than 3% of all other isotopologues combined, including a form that lacks any deuterium. In certain aspects, the compound contains less than "X"% of all other isotopologues combined, including a form that lacks any deuterium; where X is any number between 0 and 10 (e.g., 1, 0.5, 0.001), inclusive. Compositions of matter that contain greater than 10% of all other isotopologues combined are referred to herein as "mixtures" and must meet the parameters set forth below. These limits of isotopic composition and all references to isotopic composition herein, refer solely to the relative amounts of deuterium/hydrogen present in the active, free base form of the compound of the formulae herein (e.g., Formula I), and do not include the isotopic composition of hydrolyzable portions of prodrugs, or of counterions.

The term "isotopologue" refers to species that differ from a specific compound of this invention only in the isotopic composition of their molecules or ions.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as paratoluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

The compounds of the present invention may contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present Methods of obtaining or synthesizing diastereomers are well known in the art and may be applied as practicable to final compounds or to starting material or intermediates. Other embodiments are those wherein the compound is an isolated compound. The term "at least X% enantiomerically enriched" as used herein means that at least X% of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

The terms "lighter isotopologue" and "lighter atom isotopologue" as used herein, refer to species that differ from a specific compound of this invention in that they comprise hydrogen at positions occupied by a deuterium in the specific compound.

A specific compound of this invention may also be referred to as a "heavy atom isotopic compound" to distinguish it from its lighter isotopologues when discussing mixtures of isotopologues.

The term "heavy atom" refers to isotopes of higher atomic weight than the predominant naturally occurring isotope.

The term "stable heavy atom" refers to non-radioactive heavy atoms.

"D" refers to deuterium.

"Stereoisomer" refers to both enantiomers and diastereomers.

"Tert", "$^t$", and "t-" each refer to tertiary.

"US" refers to the United States of America.

"FDA" refers to Food and Drug Administration.

"NDA" refers to New Drug Application.

Throughout this specification, reference to "each Y" includes, independently, all "Y" groups (e.g., $Y^{1a}$, $Y^{1b}$, $Y^{1c}$, $Y^{2a}$, $Y^{2b}$, and $Y^{2c}$) where applicable. Throughout this specification, reference to "each Z" includes, independently, all "Z" groups (e.g., $Z^{1a}$, $Z^{1b}$, $Z^{2a}$, and $Z^{2b}$) where applicable.

Therapeutic Compounds

In one embodiment, the present invention provides a compound of formula I:

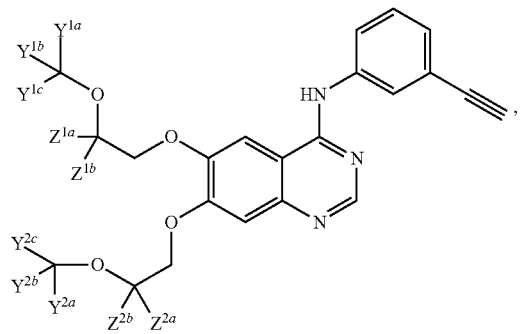

Formula I

Formula I, or a pharmaceutically acceptable salt of said compound, wherein:

each Y (e.g., $Y^{1a}$, $Y^{1b}$, $Y^{1c}$, $Y^{2a}$, $Y^{2b}$, and $Y^{2c}$) is independently selected from hydrogen or deuterium;

each Z (e.g., $Z^{1a}$, $Z^{1b}$, $Z^{2a}$, and $Z^{2b}$) is independently selected from hydrogen or deuterium;

and at least one Y or Z is deuterium.

In one embodiment, the invention provides a compound of formula I, wherein $Y^{1a}$, $Y^{1b}$, and $Y^{1c}$ are simultaneously deuterium. In another embodiment, the invention provides a compound of formula I, wherein $Y^{2a}$, $Y^{2b}$ and $Y^{2c}$ are simultaneously deuterium. In still another embodiment, the invention provides a compound of formula I, wherein $Y^{1a}$, $Y^{1b}$, $Y^{1c}$, $Y^{2a}$, $Y^{2b}$ and $Y^{2c}$ are simultaneously deuterium.

In certain embodiments, the invention provides a compound of formula I, wherein each $Z^1$ is the same; and each $Z^2$ is the same.

In another embodiment, the invention provides a compound of formula I, wherein $Z^{1a}$ and $Z^{1b}$ are simultaneously deuterium.

In another embodiment, the invention provides a compound of formula I, wherein $Z^{2a}$ and $Z^{2b}$ are simultaneously deuterium.

In another embodiment, the invention provides a compound of formula I, wherein $Z^{1a}$, $Z^{1b}$, $Z^{2a}$ and $Z^{2b}$ are simultaneously deuterium.

Specific compounds of Formula I include those delineated in Table 1 below.

TABLE 1

| Cmpd | $Y^{1a}$ | $Y^{1b}$ | $Y^{1c}$ | $Y^{2a}$ | $Y^{2b}$ | $Y^{2c}$ | $Z^{1a}$ | $Z^{1b}$ | $Z^{2a}$ | $Z^{2b}$ |
|---|---|---|---|---|---|---|---|---|---|---|
| 101 | D | D | D | H | H | H | H | H | H | H |
| 102 | H | H | H | D | D | D | H | H | H | H |
| 103 | H | H | H | H | H | H | D | D | H | H |
| 104 | H | H | H | H | H | H | H | H | D | D |
| 105 | D | D | D | D | D | D | H | H | H | H |
| 106 | H | H | H | H | H | H | D | D | D | D |
| 107 | D | D | D | H | H | H | D | D | H | H |
| 108 | H | H | H | D | D | D | H | H | D | D |
| 109 | D | D | D | D | D | D | D | D | D | D |

In another embodiment, the invention provides a compound of Formula IA:

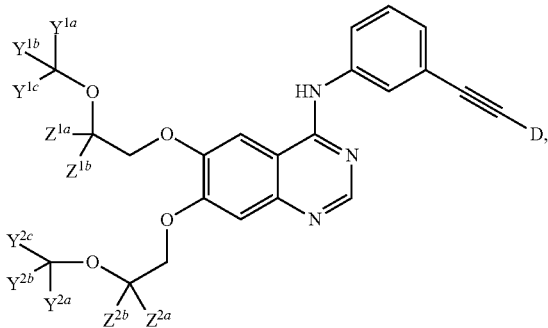

wherein each Y (e.g., $Y^{1a}, Y^{1b}, Y^{1c}, Y^{2a}, Y^{2b}, Y^{2c}$) and each Z (e.g., $Z^{1a}, Z^{1b}, Z^{2a}$ and $Z^{2b}$) is independently selected from hydrogen and deuterium.

In one embodiment, the invention provides a compound of Formula IA, wherein each $Y^1$ is the same; and each $Y^2$ is the same. In one specific embodiment, $Y^{1a}$, $Y^{1b}$, and $Y^{1c}$ are simultaneously deuterium. In another specific embodiment, $Y^{2a}$, $Y^{2b}$ and $Y^{2c}$ are simultaneously deuterium. In still another specific embodiment, $Y^{1a}, Y^{1b}, Y^{1c}, Y^{2a}, Y^{2b}$ and $Y^{2c}$ are simultaneously deuterium.

In certain embodiments, the invention provides a compound of Formula IA, wherein each $Z^1$ is the same; and each $Z^2$ is the same. In a specific embodiment $Z^{1a}$ and $Z^{1b}$ are simultaneously deuterium. In another specific embodiment, $Z^{2a}$ and $Z^{2b}$ are simultaneously deuterium. In still another specific embodiment, $Z^{1a}$, $Z^{1b}$, $Z^{2a}$ and $Z^{2b}$ are simultaneously deuterium.

In still another specific embodiment of Formula IA, each Y and each Z is simultaneously hydrogen.

Specific compounds of Formula IA include those delineated in Table 1 below.

In another set of embodiments, any atom not designated as deuterium in any of the embodiments set forth above is present at its natural isotopic abundance.

In an even more specific embodiment, the compound of this invention is selected from:

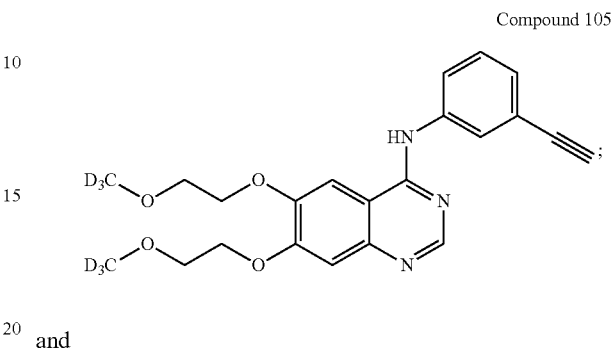

Compound 105 and

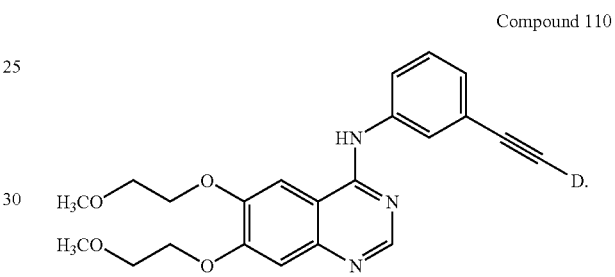

Compound 110

The synthesis of compounds of the formulae herein (e.g., Formula I and IA) can be readily effected by synthetic chemists of ordinary skill. Relevant procedures and intermediates are disclosed, for instance, in U.S. Pat. No. 5,747,498, EP 1,110,953, EP 817,775, and U.S. Pat. No. 6,476,040. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Convenient methods for producing compounds of Formula I are described in Schemes 1-7. In each of the schemes set forth below, asterisks (*) are used to designate optional deuteration sites, each "P" is used to designate an independently selected protecting group (e.g., nitrogen-protecting group, tBOC, benzyl, acyl), and each "L" is used to designate a displaceable group. A suitable displaceable group L is, for example, a halogen, alkoxy, aryloxy or sulfonyloxy group, for

TABLE 2

| Cmpd | $Y^{1a}$ | $Y^{1b}$ | $Y^{1c}$ | $Y^{2a}$ | $Y^{2b}$ | $Y^{2c}$ | $Z^{1a}$ | $Z^{1b}$ | $Z^{2a}$ | $Z^{2b}$ | W |
|---|---|---|---|---|---|---|---|---|---|---|---|
| 110 | H | H | H | H | H | H | H | H | H | H | D |
| 111 | D | D | D | H | H | H | H | H | H | H | D |
| 112 | H | H | H | D | D | D | H | H | H | H | D |
| 113 | H | H | H | H | H | H | D | D | H | H | D |
| 114 | H | H | H | H | H | H | H | H | D | D | D |
| 115 | D | D | D | D | D | D | H | H | H | H | D |
| 116 | H | H | H | H | H | H | D | D | D | D | D |
| 117 | D | D | D | H | H | H | D | D | H | H | D |
| 118 | H | H | H | D | D | D | H | H | D | D | D |
| 119 | D | D | D | D | D | D | D | D | D | D | D | example a chloro, bromo, methoxy, phenoxy, methanesulfonyloxy or toluene-4-sulfonyloxy group. Each R is an H, alkyl, alkoxyalkyl or protecting group.

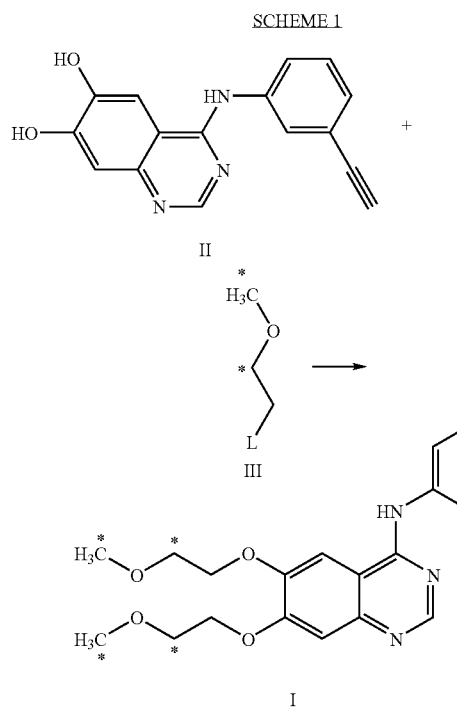

Scheme 1 shows the coupling of a quinazoline intermediate (II), with an alkoxy intermediate (III), in the presence of a suitable base, such as potassium carbonate, to form the compound of formula I. In alternate versions, the hydrogen atom on the aniline nitrogen of II may be optionally replaced by a protecting group.

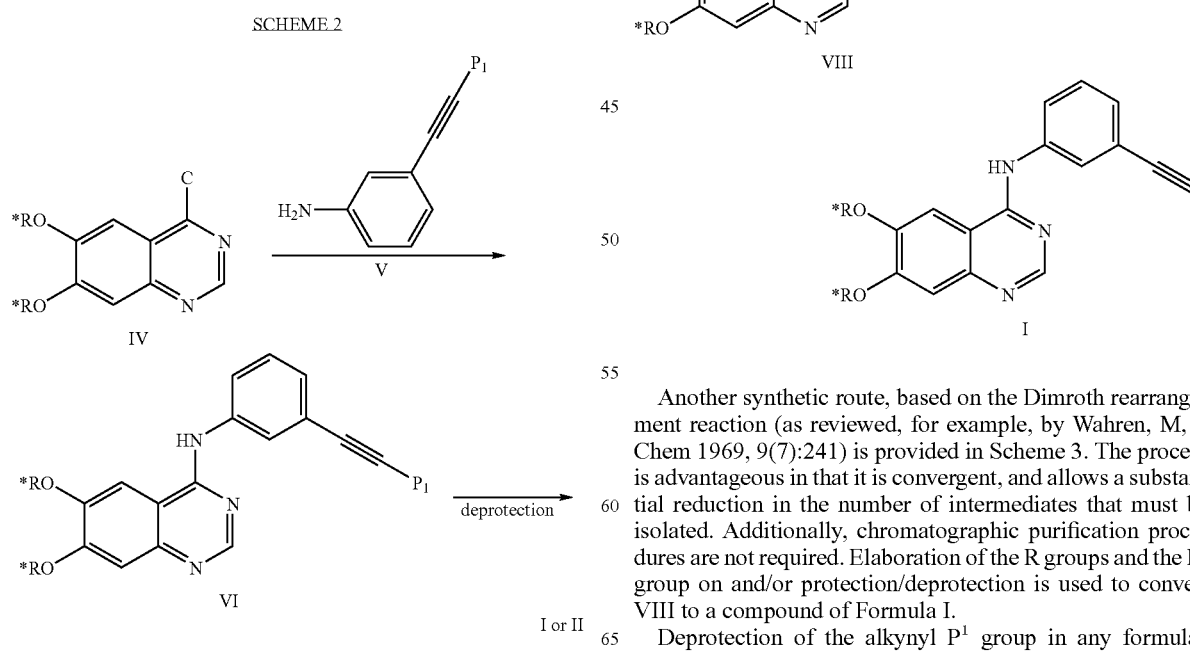

The compound II is synthesized by the reaction steps shown in Scheme 2. Quinazolinone IV is reacted with a compound of formula V in the presence of heat, acid, or base, to form VI. Deprotection, if necessary, provides intermediate II. When R is an alkoxyalkyl, appropriate deprotection of the alkynyl $P^1$ provides compounds of formula I directly. Compound V can be prepared from the corresponding nitro compound, by standard reduction (e.g., hydrogenation, $H_2$ gas with catalyst (e.g., 5% platinum on alumina), which can be prepared by alkyne-aryl coupling (e.g., palladium (II) mediated coupling of 1-bromo-3-nitrobenzene and triethylsilylacetylene). See, for example U.S. Pat. No. 6,476,040.

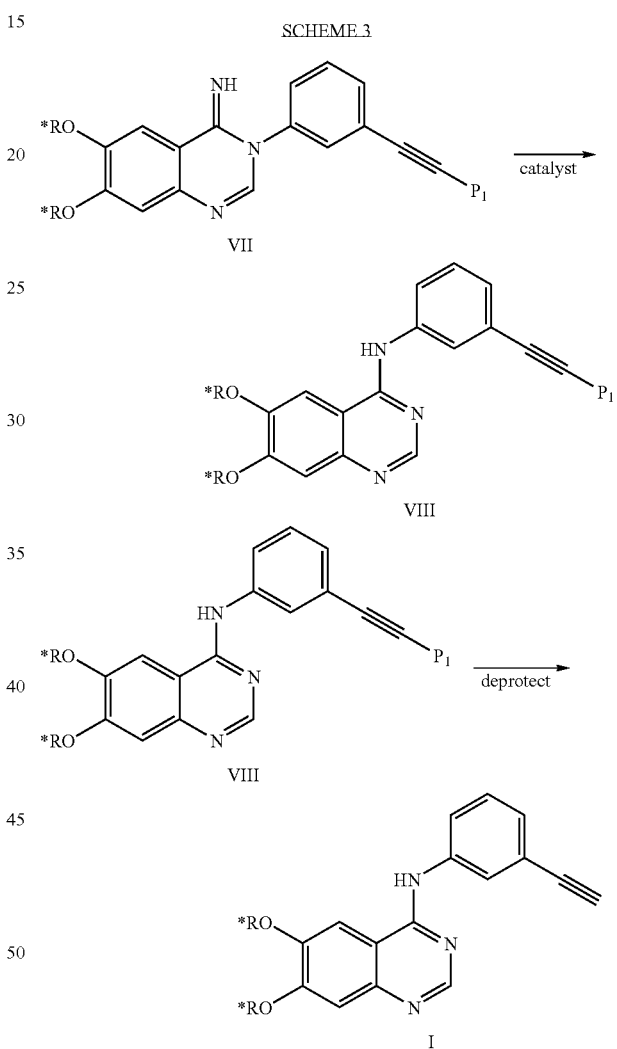

Another synthetic route, based on the Dimroth rearrangement reaction (as reviewed, for example, by Wahren, M, Z Chem 1969, 9(7):241) is provided in Scheme 3. The process is advantageous in that it is convergent, and allows a substantial reduction in the number of intermediates that must be isolated. Additionally, chromatographic purification procedures are not required. Elaboration of the R groups and the $P^1$ group on and/or protection/deprotection is used to convert VIII to a compound of Formula I.

Deprotection of the alkynyl $P^1$ group in any formulae herein (e.g., Formula VIII) can be, for example, by treatment with an alkali metal or alkaline metal hydroxide where $P^1$ is —C(OH)dialkyl; or by tetraalkylammonium fluoride treatment where $P^1$ is trialkyl-(or alkyldiaryl-) silyl.

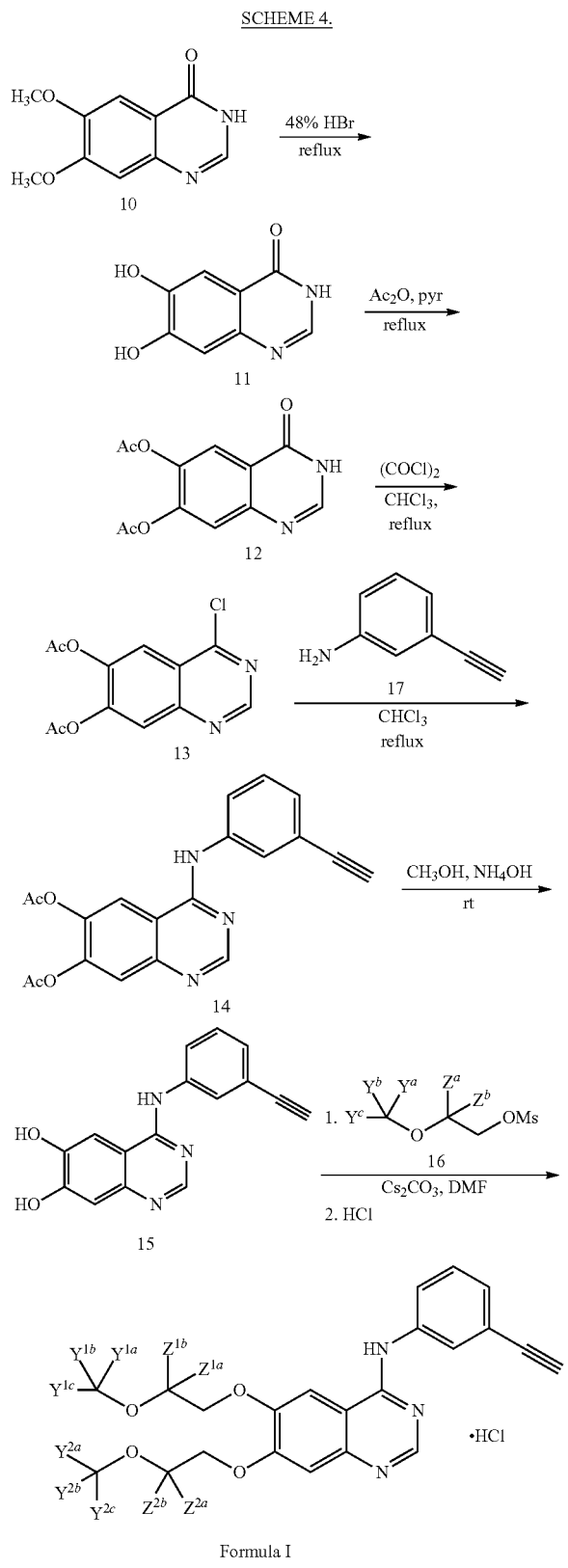

Scheme 4 shows an alternate route to a compound of Formula I, wherein the dimethoxyquinazolinone 10 is demethylated to the dihydroxyquinazolinone 11 by heating in hydrobromic acid. Dihydroxyquinazolinone 11 is then acetylated with acetic anhydride to form the corresponding diacetylquinazolinone 12 which is halogenated with oxalyl chloride to form the chloroquinazoline 13. Chloroquinazoline 13 is then combined with ethynyl aniline 17 to form diacetylquinazolinamine 14. Deacetylation of diacetylquinazolinamine 14 with ammonium hydroxide and methanol provides the corresponding quinazolinamine 15, which is then combined with an appropriately deuterated 2-methoxyethyl methane sulfonate 16 to form a compound of Formula I.

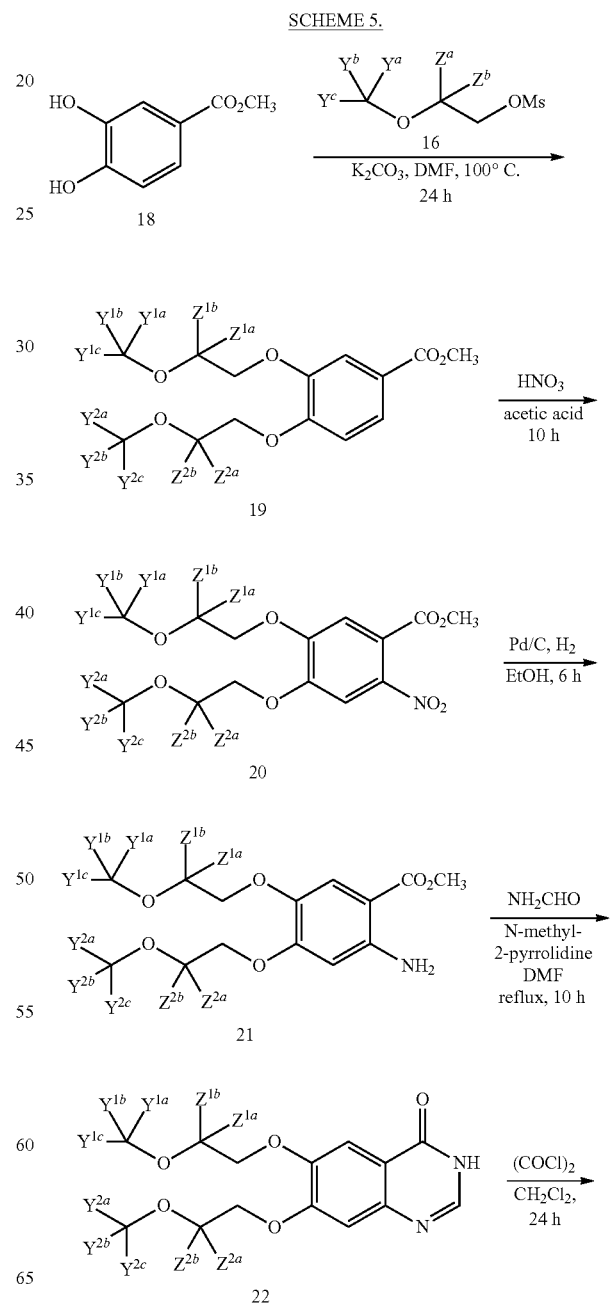

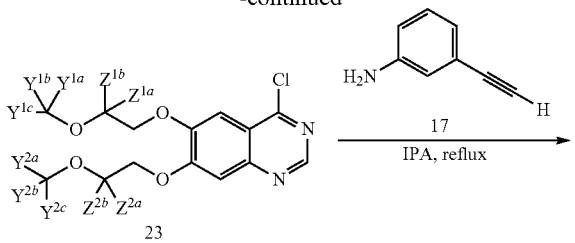

23

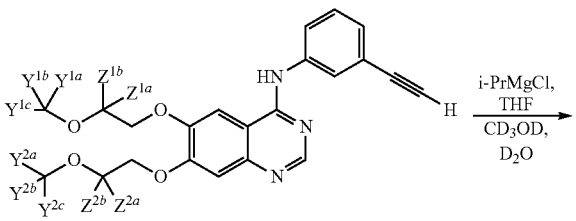

Formula I

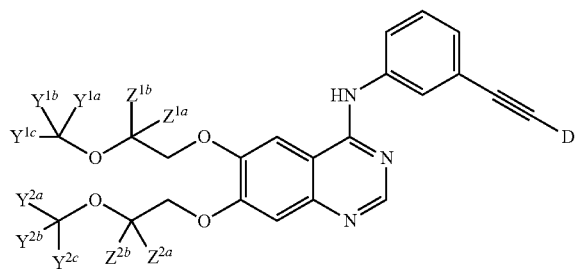

Formula IA

Scheme 5 shows a synthetic route to compounds of Formula IA. Methyl-3,4-dihydroxy benzoate 18 is combined with an appropriately deuterated 2-methoxyethyl methane sulfonate 16 to produce intermediate 19. Nitration of 19 with nitric acid and acetic acid produces the nitrobenzene compound 20. The nitrobenzene 19 is reduced to the corresponding aniline 21, which is then cyclized to quinazolinone 22. The quinazolinone 22 is chlorinated with oxalyl chloride to form the chloroquinazoline 23, which is then combined with ethynyl aniline 17 to form a compound of Formula I. Conversion to a compound of Formula IA is achieved by treatment with isopropyl magnesium chloride in the presence of $d_3$-MeOH and $D_2O$. This conversion step may be used on a compound of Formula I produced by any of Schemes 1 to 4.

For the synthesis of compounds of the invention, a suitable base when not specified is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

All reactions are preferably carried out in the presence of a suitable inert solvent or diluent, which, if not specified is selected for example from an aromatic solvent such as toluene, a xylene, cumene or chlorobenzene, an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, a polar aprotic solvent such as acetonitrile, propionitrile, butyronitrile, ethyl acetate, tetrahydrofuran or 1,4-dioxan, or a dipolar aprotic solvent such as N,N-dimethylformamide, N,N-dimethylacetamide, N-methylpyrrolidin-2-one or dimethylsulfoxide. A further suitable solvent or diluent is water or a polar protic solvent such as a primary, secondary or tertiary alkyl alcohol, for example, methanol, ethanol, a butanol or pentanol. Mixtures of such suitable solvents or diluents may be used.

If not specified, the reactions are conveniently carried out at a temperature in the range, for example, about 10° C. to about 250° C., preferably in the range 20° C. to 100° C. In certain instances, the reaction temperature is the reflux temperature of the reaction solvent or diluent or mixture thereof. For example, when the solvent or diluent is an aromatic solvent such as toluene, a xylene or cumene, or a mixture thereof, the reaction temperature is in the range, for example, 80 to 250° C., conveniently in the range, for example, 100 to 170° C. or in the range, for example, 100 to 140° C., more conveniently at or near 110° C. or at or near 130° C. In the Dimroth reaction, a suitable elevated temperature is, for example, a temperature in the range, for example, 40 to 250° C.

In one aspect of the invention, the rearrangement reaction is carried out under substantially anhydrous conditions. In such a case, a convenient solvent or diluent is, for example, an aromatic solvent such as toluene or a xylene, or mixtures thereof.

If not otherwise indicated, the quinazoline derivative of the formula I may be obtained from the processes set forth above in the form of the free base or in the form of a salt with the acid of the formula H-L wherein L has the meaning defined hereinbefore. When it is desired to obtain the free base from the salt, the salt may be treated with a suitable base as defined hereinbefore using a conventional procedure. Salts include but are not limited to, the hydrochloride salt, dihydrochloride salt, (+)-tartaric acid salt, difumaric acid salt, citric acid salt, dimethane sulfonic acid salt, disulfuric acid salt, and di-4-toluene sulfonic acid salt.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, R, R', X, etc.) or not. The suitability of a chemical group in a compound structure for use in synthesis of another compound structure is within the knowledge of one of ordinary skill in the art.

Additional methods of synthesizing compounds of the formulae herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

The invention further provides a mixture of a compound of this invention and its lighter isotopologues. These mixtures may occur, for instance, simply as the result of an inefficiency of incorporating the isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More preferable is a mixture comprising at least 80% of the heavy atom isotopic compound. Most preferable is a mixture comprising 90% of the heavy atom isotopic compound. In one aspect, is a mixture at least about "X"% of the heavy atom isotopic compound (i.e., less than about X% of lighter isotopologues), where X is a number between 0 and 100, inclusive.

Compositions

The invention also provides compositions comprising an effective amount of a compound of the formulae herein (e.g., Formula I), or a pharmaceutically acceptable salt, of said compound; and an acceptable carrier. In one embodiment, the composition is a pyrogen-free composition. In another embodiment, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

A specialized formulation for compounds of the formulae herein (e.g., Formula I or IA) is a nanoparticulate formulation as disclosed for example in WO 2006110811.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

The size of the dose required for the therapeutic or prophylactic treatment of a particular proliferative disease will necessarily be varied depending on the subject treated, the route of administration, and the severity of the illness being treated. Such dosages can be found in U.S. Pat. No. 5,770,599. The compounds of the invention will normally be administered to a subject at a unit dose within the range of about 5 mg to about 10,000 mg per square meter body area of the subject, i.e. from about 0.1 mg/kg to about 200 mg/kg, providing a therapeutically-effective dose. A unit dose form such as a tablet or capsule will usually contain, for example from about 1 mg to about 250 mg of active ingredient. Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of the present invention further comprises a second therapeutic agent. The second therapeutic agent includes any compound or therapeutic agent known to have or that demonstrates advantageous properties when administered with erlotinib. Such agents are described in detail in U.S. Pat. No. 5,770,599; WO 2001/076586; WO 2002/005791; WO 2001/070255; WO 2003/088971; WO 2004/014426; WO 2005/000213; WO 2005/004872; WO 2005/046665; WO 2005/052005; WO 2005/117888; WO 2006/026313; WO 2004/035057; and WO 2006/099396; the disclosures of which are incorporated herein by reference.

In one embodiment, the second therapeutic agent is selected from 2-deoxy-2-[18F]fluoro-D-glucose, 3'-deoxy-3'-[18F]fluorothymidine, 5-fluorouracil, AV412, avastin, bevacizumab, bexarotene, bortezomib, calcitriol, canertinib, capecitabine, carboplatin, celecoxib, cetuximab, CHR-2797, cisplatin, dasatinib, digoxin, enzastaurin, etoposide, everolimus, fulvestrant, gefitinib, gemcitabine, genistein, imatinib, irinotecan, lapatinib, lenalidomide, letrozole, leucovorin, matuzumab, oxaliplatin, paclitaxel, panitumumab, pegfilgrastim, pegylated alfa-interferon, pemetrexed, Polyphenon® E, satraplatin, sirolimus, sorafenib, sutent, sulindac, sunitinib, taxotere, temodar, temozolomide, temsirolimus, TG01, tipifarnib, trastuzumab, valproic acid, vinflunine, volociximab, vorinostat, and XL647.

In a more specific embodiment, the second therapeutic agent is bevacizumab.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from a daily dose in the range of from about 1 mg/kg to about 100 mg/kg is employed. In certain embodiments, a compound of the invention or a pharmaceutically-acceptable salt thereof, will be administered at a daily dose of about 1 mg/kg to about 20 mg/kg; preferably about 1 mg/kg to about 5 mg/kg is employed. In certain embodiments, a unit dose in the range of about 1 mg/kg to about 200 mg/kg, preferably about 1 mg/kg to about 100 mg/kg, more preferably about 1 mg/kg to about 10 mg/kg, is envisaged.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for erlotinib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

If the second therapeutic agents referenced above act synergistically with the compounds of this invention it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease that is beneficially treated by erlotinib comprising the step of administering to the subject in need thereof an effective amount of a compound or a composition of this invention. Such diseases are well known in the art and are disclosed, for example, in U.S. Pat. No. 5,770,599, U.S. Pat. No. 5,747,498, EP 1,110,953, EP 817,775, and U.S. Pat. No. 6,476,040. In particular, the invention provides a method of treating a subject suffering from or susceptible to cancer, inflammation, angiogenesis, vascular restenosis, immunological disorder, pancreatitis, kidney disease, blastocyte maturation and implantation, psoriasis, or benign prostatic hypertrophy (BPH).

In a more specific embodiment, the cancer is selected from non-small cell lung cancer, ovarian cancer, colorectal cancer, head and neck cancer, brain cancer, bladder cancer, sarcoma, prostate cancer, melanoma, cervical cancer, solid tumors, astrocytoma, breast cancer, pancreatic cancer, glioblastoma multiform, renal cancer, digestive/gastrointestinal cancer, liver cancer, and gastric cancer.

In an even more specific embodiment, the cancer is non-small cell lung cancer.

The compounds of the invention also have utility in the treatment of additional disorders of cellular growth in which aberrant cell signaling by way of receptor tyrosine kinase enzymes or non-receptor tyrosine kinase enzymes, including as yet unidentified tyrosine kinase enzymes, are involved. Such disorders include, for example, inflammation, angiogenesis, vascular restenosis, immunological disorder, pancreatitis, kidney disease and blastocyte maturation and implantation. Additionally, the compounds of the invention can be used to treat other diseases involving excessive cellular proliferation such as psoriasis and benign prostatic hypertrophy (BPH).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with erlotinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include a method of treating a patient suffering from or susceptible to cancer comprising the step of co-administering a compound of Formula I and a second therapeutic agent selected from 2-deoxy-2-[18F]fluoro-D-glucose, 3'-deoxy-3'-[18F]fluorothymidine, 5-fluorouracil, AV412, avastin, bevacizumab, bexarotene, bortezomib, calcitriol, canertinib, capecitabine, carboplatin, celecoxib, cetuximab, CHR-2797, cisplatin, dasatinib, digoxin, enzastaurin, etoposide, everolimus, fulvestrant, gefitinib, gemcitabine, genistein, imatinib, irinotecan, lapatinib, lenalidomide, letrozole, leucovorin, matuzumab, oxaliplatin, paclitaxel, panitumumab, pegfilgrastim, pegylated alfa-interferon, pemetrexed, Polyphenon® E, satraplatin, sirolimus, sorafenib, sutent, sulindac, sunitinib, taxotere, temodar, temozolomide, temsirolimus, TG01, tipifamib, trastuzumab, valproic acid, vinflunine, volociximab, vorinostat, and XL647 to the patient in need thereof.

In a more specific embodiment, the co-administered second therapeutic agent is bevacizumab.

In an even more specific embodiment, the co-administered second therapeutic agent is bevacizumab and the patient is suffering from non-small cell lung cancer.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In another aspect, the invention provides the use of a compound of the formulae herein, or a pharmaceutically-acceptable salt thereof, in the manufacture of a medicament for use in the production of an anti-proliferative effect in a subject.

In another embodiment, the invention provides a method of modulating the activity of cell surface tyrosine receptor kinases, including epidermal growth factor receptor kinases (EGFR), in a cell comprising contacting the cell with one or more compounds of any of the formulae herein.

In yet another aspect, the invention provides the use of a compound of the formulae herein (e.g., Formula I or IA) alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

Diagnostic Methods and Kits

The compounds and compositions of this invention are also useful as reagents in methods for determining the concentration of erlotinib in solution or biological sample such as plasma, examining the metabolism of erlotinib and other analytical studies.

According to one embodiment, the invention provides a method of determining the concentration, in a solution or a biological sample, of erlotinib, comprising the steps of:

adding a known concentration of a compound of Formula I or IA to the solution of biological sample;

subjecting the solution or biological sample to a measuring device that distinguishes erlotinib from a compound of Formula I or IA;

calibrating the measuring device to correlate the detected quantity of the compound of Formula I or IA with the known concentration of the compound of Formula I or IA added to the biological sample or solution; and measuring the quantity of erlotinib in the biological sample with said calibrated measuring device; and determining the concentration of erlotinib in the solution of sample using the correlation between detected quantity and concentration obtained for a compound of Formula I or IA.

Measuring devices that can distinguish erlotinib from the corresponding compound of Formula I or IA include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I or IA comprising the steps of contacting the compound of Formula I or IA with a metabolizing enzyme source for a period of time and comparing the amount of the compound of Formula I or IA with the metabolic products of the compound of Formula I or IA after the period of time.

In a related embodiment, the invention provides a method of evaluating the metabolic stability of a compound of Formula I or IA in a patient following administration of the compound of Formula I or IA. This method comprises the steps of obtaining a serum, urine or feces sample from the patient at a period of time following the administration of the compound of Formula I or IA to the subject; and comparing the amount of the compound of Formula I or IA with the metabolic products of the compound of Formula I or IA in the serum, urine or feces sample.

The present invention also provides kits for use to treat non-small cell lung cancer, ovarian cancer, colorectal cancer, head and neck cancer, brain cancer, bladder cancer, sarcoma, prostate cancer, melanoma, cervical cancer, solid tumors, astrocytoma, breast cancer, pancreatic cancer, glioblastoma multiform, renal cancer, digestive/gastrointestinal cancer, liver cancer, or gastric cancer. These kits comprise (a) a pharmaceutical composition comprising a compound of Formula I or IA or a pharmaceutically acceptable salt thereof, wherein said pharmaceutical composition is in a container; and (b) instructions describing a method of using the pharmaceutical composition to treat the cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of 2-d$_3$-methoxyethyl methane sulfonate 16

Reagent 16 is prepared according to the following Scheme.

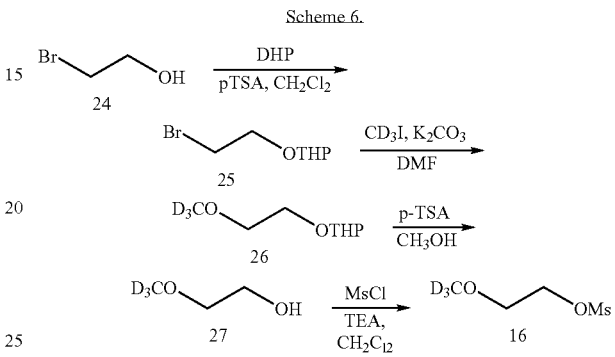

Scheme 6.

Synthesis of 2-(2-bromoethoxy)tetrahydro-2H-pyran (25). To a solution of 2-bromoethanol 24 (50.0 g, 40 mmol) in methylene chloride (500 mL) cooled to 0° C. was added 3,4-dihydro-2H-pyran (40.32 g, 48 mmol) followed by p-TSA.H$_2$O (100 mg) was added. Reaction mixture was stirred at 0° C. for 5.0 h. The reaction mixture was washed with aq NaHCO$_3$ and brine, dried over Na$_2$SO$_4$ and evaporated to give the product 25 (75.0 g, 90%). This crude product was taken to next step without purification.

Synthesis of 2-(2-d$_3$-methoxyethoxy)tetrahydro-2H-pyran (26). To a solution of 2-(2-bromoethoxy)tetrahydro-2H-pyran, 25 (40.0 g, 24.3 mmol) in DMF (100 mL) was added K$_2$CO$_3$ (40.24 g, 48.0 mmol) and CD$_3$I (4.23 g, 29.2 mmol) and stirred at 60° C. for 12.0 h. The reaction mixture was poured into cold water and extracted with diethyl ether (2×150 mL). Combined organic extracts were washed with brine, dried over Na$_2$SO$_4$ and concentrated under reduced pressure to give the product 26 (11.50 g, 37%).

Synthesis of 2-d$_3$-methoxy ethanol (27). To a solution of 2-(2-d$_3$-methoxyethoxy)tetrahydro-2H-pyran, 26 (11.0 g, 6.77 mmol) in methanol (25 mL) was added p-TSA.H$_2$O (100 mg). The resulting mixture was stirred at room temperature for 10.0 h. Methanol was distilled at atmospheric pressure and the residue was distilled at 140° C. to give the 2-d$_3$-methoxy ethanol, 27 (3.00 g, 57%).

Synthesis of 2-d$_3$-methoxyethyl methane sulfonate (16). To a 0° C. cooled solution of 2-d$_3$-methoxyethanol, 27 (2.80 g, 36.8 mmol) and triethyl amine (4.80 mL) in methylene chloride (50 mL) was added methane sulfonylchloride (4.10 g, 37 mmol) was added and stirred at 0° C. for 2.0 h. The reaction mixture was washed with aq NaHCO$_3$ and brine, dried over Na$_2$SO$_4$ and concentrated under reduced pressure to give the product (3.05 g, 55%). $^1$H NMR (CDCl$_3$): 2.94 (s, 3H), 3.66 (m, 2H), 3.80 (t, 2H).

Example 2

N-(3-ethynylphenyl)-6,7-bis(2-d$_6$-methoxyethoxy) quinazolin-4-amine hydrochloride Compound 105 is prepared according to Scheme 4 above.

Synthesis of 6,7-dihydroxy-4(3H)-quinazolinone (11). To 6,7-dimethoxy-4(3H)-quinazolinone, 10 (3.0 g, 14.5 mmol) was added 48% HBr (36 mL) and the solution was heated to reflux at 100° C. for 12 h. The reaction mixture was cooled to room temperature and the solids were filtered. The solid obtained was neutralized with aq. NH$_3$ (pH=8) and the solution was filtered and washed with water and dried to give 6,7-dihydroxy-4(3H)-quinazolinone, 11 as a off-white crystalline solid (2.20 g, 84%).

Synthesis of 6,7-diacetoxy-4(3H)-quinazolinone (12). To 6,7-dihydroxy-4(3H)-quinazolinone, 11 (2.20 g, 12.2 mmol) was added Ac$_2$O (13.3 ml) and a drop of pyridine and the reaction mixture was heated to reflux at 120° C. for 2 h. The reaction mixture was cooled to room temperature and the solvent was distilled off under reduced pressure. The residue was taken up in water and stirred for an hour at room temperature. The solid obtained was filtered and dried to give 6,7-diacetoxy-4(3H)-quinazolinone 12 as an off-white crystalline solid (1.70 g, 53%).

Synthesis of 4-chloroquinazoline-6,7-diyl diacetate (13). To a solution of 6,7-diacetoxy-4(3H)-quinazolinone, 12 (3.20 g, 11.42 mmol) in CHCl$_3$ (60 ml) was added oxalyl chloride (2.2 ml, 17.3 mmol) dropwise at 0° C. The resulting reaction mixture was stirred at room temperature for 15 minutes then was gradually heated to reflux for 5 h during which time the starting material was consumed. The reaction mixture was cooled to 10° C. and the solution was quenched with aq sodium bicarbonate. The organic layer was separated and washed with brine then dried over Na$_2$SO$_4$ and directly taken to the next step without concentration.

Synthesis of N-(3-ethynylphenyl)-6,7-diacetoxy-4-quinazolinamine hydrochloride (14). To the organic layer of the previous step was added ethynyl aniline 17 (1.19 ml, 11.42 mmol) and the reaction mixture was heated to reflux overnight. The reaction mixture was cooled to room temperature and the solution was filtered to give N-(3-ethynylphenyl)-6,7-diacetoxy-4-quinazolinamine hydrochloride, 14 as a solid (3.0 g, 94%).

Synthesis of N-(3-ethynylphenyl)-6,7-dihydroxy-4-quinazolinamine hydrochloride (15). To the hydrochloride salt, 14 (4.2 g, 11.62 mmol) in methanol (30 ml) was added 25% aqueous ammonia (4.73 ml) and the solution was stirred for 4 h. The reaction mass was filtered and the solid was washed with water to give the N-(3-ethynylphenyl)-6,7-dihydroxy-4-quinazolinamine hydrochloride, 15 (3.0 g, 93%) as a brownish yellow solid. $^1$H NMR (400 MHz, DMSO-d$_6$): 4.2 (s, 1H), 7.10 (s, 1H), 7.17-7.19 (m, 2H), 7.34-7.39 (t, 1H), 7.79 (s, 1H), 7.87-7.89 (d, 1H), 8.05 (s, 1H), 8.45 (s, 1H), 9.4-9.6 (bs. s, 1H). MS (ESI): 278.

Synthesis of N-(3-ethynylphenyl)-6,7-bis(2-d$_6$-methoxyethoxy)quinazolin-4-amine hydrochloride (Compound 105). A solution of N-(3-ethynylphenyl)-6,7-dihydroxy-4-quinazolinamine 15 (250 mg, 0.89 mmol), 2-d$_3$-methoxyethyl methane sulfonate 16 (0.83 g, 5.34 mmol), and cesium carbonate (1.70 g, 5.34 mmol) in DMF (10 mL) was heated to 60° C. for 12 h. The reaction mixture was cooled to room temperature and poured into cold water, extracted with ethyl acetate (2×20 mL) and the combined organic layer were washed with water and brine, dried over Na$_2$SO$_4$ and concentrated to give Compound 105 (150 mg). MS (ESI): 400.

Example 3

Synthesis of N-(3-di-ethynylphenyl)-6,7-bis(2-methoxyethoxy) quinazolin-4-amine hydrochloride (Compound 110)

Compound 110 was synthesized according to Scheme 5 above.

Synthesis of methyl 3,4-bis(2-methoxyethoxy)benzoate (19). A solution of methyl 3,4-dihydroxybenzoate (18, 10.0 g, 64.88 mmol), 2-methoxyethyl methane sulfonate 16 (59.95 g, 389.3 mmol), potassium carbonate (54.06 g, 389.30 mmol), sodium iodide (58.35 g, 389.3 mmol) in DMF (100 mL) was heated to 100° C. Reaction progress was monitored by TLC and after 12.0 h the reaction was found to be complete. The reaction mixture was cooled to room temperature and poured in to cold water. Extracted with ethyl acetate (2×150 mL) and the combined organic layer were washed with water and brine. Dried over Na$_2$SO$_4$ and evaporated to give compound 19.

Synthesis of methyl 3,4-bis(2-methoxyethoxy)benzoate (20). To a solution of compound 19 (17.0 g, 59.79 mmol) in acetic acid (57.8 mL) was added dropwise nitric acid (18.3 mL, 70%) at 0-5° C. and this mixture was stirred at room temperature. Reaction was monitored by HPLC @254 nm and after 10.0 h the reaction was complete. Reaction mixture was poured on cold water (100 mL) and extracted with ethyl acetate (3×150 mL). The combined organic extracts were washed with aq NaHCO$_3$ (2×100 mL) and brine. Dried over Na$_2$SO$_4$ and evaporated to give compound 20.

Synthesis of methyl 2-amino-4,5-bis(2-methoxyethoxy) benzoate (21). A solution of compound 20 (17.0 g, 51.62 mmol) in ethanol (150 mL) was added 10% Pd—C (1.70 g) and subjected to hydrogenation in a parr apparatus (50 psi) at room temperature. Reaction was monitored by TLC. After 12.0 h TLC indicated no starting material. The catalyst was filtered off by using a celite plug and washed with ethanol (50 mL). Solvent was removed was removed under reduced pressure to afford compound 21 as brown slurry Synthesis of 6,7-bis(2-methoxyethoxy)quinazolin-4(3H)-one (22). Formamide (130 mL) was added to a solution of compound 21 (13.0 g, 43.43 mmol) in N-methyl-2-pyrrolidone (130 mL) and the reaction mixture was heated to 165-170° C. under N$_2$ for 12 h. Reaction was monitored by TLC. After 8.0 h TLC indicated no starting material. The reaction mixture was poured in to ice cold water and solids were filtered. The crude product was purified by column chromatography to give compound 22 as light yellow solid.

Synthesis of 4-chloro-6,7-bis(2-methoxyethoxy)quinazoline (23). To a solution of compound 22 (2.60 g, 8.83 mmol) in dichloromethane (25 mL), was added a drop of N,N-Dimethyl formamide and to that oxalyl chloride (1.52 mL, 17.669 mmol) was added dropwise. This mixture was stirred at room temperature for 12 h. Reaction was monitored by TLC and the reduction continued until TLC indicated no starting material.

The reaction mixture was poured in to water. Extracted with ethyl acetate and the combined organic layer were washed with Sat.NaHCO₃ and brine and dried over Na₂SO₄ and evaporated to give the crude compound 23 (3.5 g, crude), which was used in the next reaction without further purification.

Synthesis of N-(3-ethynylphenyl)-6,7-bis(2-methoxyethoxy)quinazolin-4-amine(erlotinib). A solution of compound 23 (3.5 g, 11.19 mmol) in isopropanol (20 mL) was added drop wise to a solution of pyridine (0.71 mL, 8.95 mmol) and 4-ethynylphenylamine (1.17 mL, 11.19 mmol) in isopropanol (50 mL). Reaction mixture was stirred and heated to reflux under argon resulting in precipitation of orange solid. Then the reaction mixture brought to room temperature and stirred 12.0 h. The precipitate was filtered and washed with hot isopropanol and dried to yield erlotinib (1.66 g, 35%). $^1$H NMR (DMSO-$d_6$): 3.36 (s, 6H), 3.78 (s, 4H), 4.30 (s, 1H), 4.35 (t, 4H), 7.40 (d, 1H), 7.50 (t, 1H), 7.36 (d, 1H), 7.87 (s, 1H), 8.33 (s, 1H), 8.85 (s, 1H), 11.30 (s, 1H). MS: MS: ESI, m/z 394[M+H]⁺. HPLC: 98.9% (@254 nm).

Synthesis of N-(3-di-ethynylphenyl)-6,7-bis(2-methoxyethoxy)quinazolin-4-amine (Compound 110). To a −30° C. cooled solution of erlotinib (250 mg, 0.90 mmol) in THF (20 L) was added isopropyl magnesium chloride (1.6 N in THF, 2 mL). Reaction mixture was stirred at −30° C. for 3.0 h and CD₃OD (1 mL) was added and slowly brought to room temperature over a period of 2.0 h. Stirred at room temperature and reaction was monitored by MS. After 10.0 h MS showed 3% starting material. Reaction mixture was quenched with D₂O and extracted with ethyl acetate (2×25 mL). Combined organic extracts were washed with water and brine. Dried over Na₂SO₄ and evaporated to give Compound 110 (178 mg, 76%).

Example 4

Metabolism Studies

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, JB, Biochem Pharmacol, 1994, 47:1469; Iwatsubo, T et al., Pharmacol Ther, 1997, 73:147; and Lave, T, et al., Pharm Res, 1997, 14:152.

Microsomal Assay. The metabolic stability of compounds of Formula I or IA is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures. Human liver microsomes are obtained from a commercial source (e.g., XenoTech, LLC (Lenexa, Kans.)). The incubation mixtures are prepared as follows:

| Reaction Mixture Composition | |
|---|---|
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM. |

Incubation of Test Compounds with Liver Microsomes. The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH₂O to terminate the reaction. The positive controls, testosterone and propranolol, as well as erlotinib, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a compound of Formula I or IA or II in 100 mM potassium phosphate buffer (pH 7.4) was incubated at 37° C. in triplicate. Positive controls contain 1 µM of erlotinib instead of a compound of Formula I or IA. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:
1. The compound

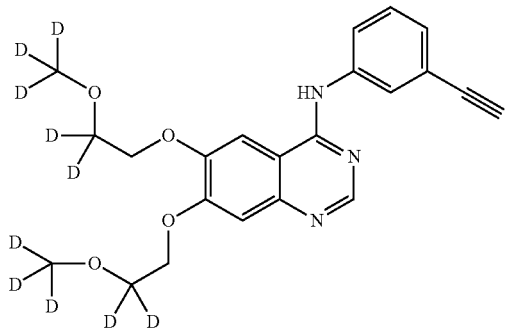 [SMILES: [2H]C([2H])([2H])OC([2H])([2H])COc1cc2ncnc(Nc3cccc(C#C)c3)c2cc1OCC([2H])([2H])OC([2H])([2H])[2H]]

or a pharmaceutically acceptable salt thereof.

2. The compound of claim 1, wherein any atom not designated as deuterium is present at its natural isotopic abundance.

3. A pyrogen-free composition comprising the compound of claim 1, and an acceptable carrier.

4. The composition of claim 3 formulated for pharmaceutical administration, wherein the carrier is a pharmaceutically acceptable carrier.

5. A method of treating a patient suffering from psoriasis, the method comprising the step of administering to the patient a composition of claim 4.

6. A method of treating a patient suffering from a disease or disorder selected from non-small cell lung cancer, ovarian cancer, colorectal cancer, head and neck cancer, brain cancer, bladder cancer, sarcoma, prostate cancer, melanoma, cervical cancer, solid tumors, astrocytoma, breast cancer, pancreatic cancer, glioblastoma multiform, renal cancer, digestive/gastrointestinal cancer, and liver cancer, the method comprising the step of administering to the patient a composition of claim 4.

7. The method of claim 6, wherein the patient is suffering from non-small cell lung cancer.

8. The method of claim 5, comprising the further step of co-administering to the patient in need thereof a second therapeutic agent useful in the treatment of a disease or disorder selected from cancer, inflammation, angiogenesis, vascular restenosis, immunological disorder, pancreatitis, kidney disease, blastocyte maturation and implantation, psoriasis, and benign prostatic hypertrophy (BPH).

9. The method of claim 8, wherein the patient is suffering from cancer and the second therapeutic agent is selected from 2-deoxy-2-[$^{18}$F]fluoro-D-glucose, 3'-deoxy-3'-[$^{18}$F]fluorothymidine, 5-fluorouracil, AV412, avastin, bevacizumab, bexarotene, bortezomib, calcitriol, canertinib, capecitabine, carboplatin, celecoxib, cetuximab, CHR-2797, cisplatin, dasatinib, digoxin, enzastaurin, etoposide, everolimus, fulvestrant, gefitinib, gemcitabine, genistein, imatinib, irinotecan, lapatinib, lenalidomide, letrozole, leucovorin, matuzumab, oxaliplatin, paclitaxel, panitumumab, pegfilgrastim, pegylated alfa-interferon, pemetrexed, satraplatin, sirolimus, sorafenib, sutent, sulindac, sunitinib, taxotere, temodar, temozolomide, temsirolimus, TG01, tipifarnib, trastuzumab, valproic acid, vinflunine, volociximab, vorinostat, and XL647.

10. The method of claim 9, wherein the second therapeutic agent is bevacizumab.

11. The method of claim 10, wherein the patient is suffering from non-small cell lung cancer.

12. The compound of claim 1, wherein each designated deuterium atom of the compound has an isotopic enrichment factor of at least 3000.

* * * * *